United States Patent
Jones et al.

(10) Patent No.: US 8,451,460 B2
(45) Date of Patent: May 28, 2013

(54) MONITORING SYSTEM FOR THE ACQUISITION OF THE LAYER THICKNESS OF DUST IN VENTILATION DUCTS

(75) Inventors: Nigel Jones, Bramfield (GB); Ron Ashby, Cannock (GB)

(73) Assignee: Vanguard Sensor Technology Limited, Hoddesdon, Hertfordshire (GB)

( * ) Notice: Subject to any disclaimer, the term of this patent is extended or adjusted under 35 U.S.C. 154(b) by 333 days.

(21) Appl. No.: 12/735,063

(22) PCT Filed: Dec. 18, 2008

(86) PCT No.: PCT/GB2008/004180
§ 371 (c)(1),
(2), (4) Date: Aug. 31, 2010

(87) PCT Pub. No.: WO2009/081109
PCT Pub. Date: Jul. 2, 2009

(65) Prior Publication Data
US 2011/0122423 A1 May 26, 2011

(30) Foreign Application Priority Data

Dec. 20, 2007 (GB) .................................. 0724779.4
Aug. 22, 2008 (GB) .................................. 0815366.0

(51) Int. Cl.
*G01B 11/06* (2006.01)

(52) U.S. Cl.
USPC ....................................... 356/631; 356/239.8

(58) Field of Classification Search
USPC ........ 356/625–632, 239.7–239.8; 250/559.27, 250/559.28
See application file for complete search history.

(56) References Cited

U.S. PATENT DOCUMENTS

| | | | | |
|---|---|---|---|---|
| 2,299,798 A | * | 10/1942 | Colson et al. | 340/323 R |
| 3,566,135 A | * | 2/1971 | Mouchart | 250/559.15 |
| 3,569,722 A | * | 3/1971 | Denson | 356/632 |
| 3,744,916 A | * | 7/1973 | Bey et al. | 356/632 |
| 4,182,259 A | * | 1/1980 | Garner et al. | 118/712 |

(Continued)

FOREIGN PATENT DOCUMENTS

| GB | 2411069 | 8/2005 |
|---|---|---|
| JP | 10170438 | 12/1996 |
| JP | 2004186733 | 11/2002 |
| JP | 2006319560 | 5/2005 |

*Primary Examiner* — Hoa Pham
(74) *Attorney, Agent, or Firm* — Stetina Brunda Garred & Brucker

(57) ABSTRACT

A monitoring system is disclosed, designed to detect the depth of deposition of a substance on a' surface (12), such as the depth of dust in a ventilation shaft. The monitoring system includes a light source (14) and a sensor (16, 30). The light source is arranged to transmit light across a detection surface and the sensor is on the other side of the detection surface. When a substance, such as dirt or grease, is deposited on the surface it obstructs the light and the amount of light reaching the sensor decreases. A processing means (26) detects the decrease in light and from this the depth of the deposition on the surface can be calculated. Preferably the sensor comprises a CCD array (32), and the substance throws a shadow on the array. The processing means can then determine the depth of the substance from the position on the array of the edge of the shadow. Preferably the monitoring system is placed in a low power 'sleep' mode in between intermittent operations for detecting the depth of the substance. In this, way, it can be battery operated and the battery life is preserved.

35 Claims, 4 Drawing Sheets

U.S. PATENT DOCUMENTS

| | | | |
|---|---|---|---|
| 4,885,709 A * | 12/1989 | Edgar et al. | 702/30 |
| 5,196,901 A * | 3/1993 | Champetier | 356/237.3 |
| 5,266,810 A * | 11/1993 | Murphy | 250/559.24 |
| 5,276,388 A * | 1/1994 | Levers | 318/444 |
| 5,319,827 A | 6/1994 | Yang | |
| 5,396,332 A * | 3/1995 | Ciszek | 356/632 |
| 5,581,354 A * | 12/1996 | Hassbjer | 356/632 |
| 5,684,574 A * | 11/1997 | Shiokawa et al. | 356/72 |
| 5,805,291 A * | 9/1998 | Calvin et al. | 356/429 |
| 5,897,611 A * | 4/1999 | Case et al. | 702/150 |
| 6,521,889 B1 | 2/2003 | Ina et al. | |
| 7,589,836 B2 * | 9/2009 | Mack | 356/239.8 |
| 2010/0225477 A1 * | 9/2010 | Livchak et al. | 340/540 |

* cited by examiner

MONITORING SYSTEM FOR THE ACQUISITION OF THE LAYER THICKNESS OF DUST IN VENTILATION DUCTS

This invention relates to apparatus for monitoring the amount of dirt on a surface. The apparatus may be used in ventilation systems.

Ventilation ducts in buildings are used to promote air flow within the building and remove waste gases. Cleaning the ducts is necessary to prevent excess build up of substances such as grease and dust within the ducts. Conventionally, ventilation ducts are cleaned at regular intervals, for example, 3 months, 6 months or annually, depending on the substances which will be deposited on their walls and how heavily the ducts are used.

As cleaning can be expensive and time consuming it is often desirable to monitor the dirt build up within the ducts so that cleaning is not carried out unnecessarily. In order to determine whether to clean a duct or not, typically, pictures or videos are taken of the inside of the duct or partial disassembly and visual inspection and/or measurement is carried out. The pictures may be used to determine whether the duct needs cleaning.

As can be appreciated this is a time consuming process and therefore it is desirable to have a more efficient way of determining when to clean a duct.

In accordance with a first aspect of the present invention there is provided a detector comprising a plate, a light source positioned to transmit light over a surface of the plate, a light sensor positioned to detect light that has been transmitted by the light source and passed over the surface of the plate and processing means arranged to determine the depth of a substance on the plate from the amount of light detected by the light sensor.

The detector advantageously includes a plurality of light sources and light sensors, each light source having a corresponding light sensor. This allows the detector to mitigate the effects of anomalies where one sensor is obstructed more than other sensors disposed throughout the duct would be.

Preferably the detector includes a reference light source and light sensor positioned a distance away from the plate such that the path of light between the reference light source and light sensor is not obstructed by the substance on the plate. This allows the effect of dust collecting on windows or a decrease in the efficacy of the light sensors/sources to be compensated for.

Optionally, the processing means is arranged to determine the depth of the substance by determining when the amount of the light detected by the light sensor is below a threshold. The threshold may be calculated as a percentage of the light received by the reference light sensor. Alternatively, the apparatus may include a reference table including the intensity of the light detected by the light sensor and the corresponding depth of substance, the processing means being arranged to consult the reference table and thereby determine the depth of the substance on the plate from the intensity of light detected by the light sensor.

Optionally, the plurality of light sources and light sensors may be disposed at differing distances from the plate; the processing means being arranged to determine the light sensors receiving an intensity of light above a threshold and use the determination to calculate the depth of the surface.

The light sensor may be a receiver array. Additionally, the processing means, if the light sensor is a receiver array may be arranged to determine the point of a step change in the light detected by the receiver array and thereby determine the depth of the substance on the surface of the plate.

Preferably, the detector includes a timer, an activation means and a deactivation means; the apparatus being arranged to turn on using the activation means and turn off using the deactivation means after a period of time has expired. The processing means may alter the period of time according to the determined depth of substance.

Optionally, the processing means is located remotely from the plate, light source and light sensor. A signal representing the light detected by the light sensor may be transmitted wirelessly to the processing means.

The processing means may be arranged to transmit the determination to a user interface. Optionally, the apparatus may include an aerial and the determination is transmitted to a user interface wirelessly.

Preferably, the light source is arranged to transmit light in pulses at a pulse frequency of 65 kHz. The light source may be arranged so that the length of a pulse is 160 microseconds.

According to another aspect of the present invention, there is provided a detector for detecting the thickness of a substance deposited on a surface, comprising: a surface on which a substance may be deposited; a light source arranged to shine light so that the light passes across the surface and, in the case that surface is clear of the substance, at least part of the light passes over the surface unobstructed; a sensor array comprising a plurality of respective light sensor elements positioned at respective different distances in a direction transverse to the surface, and at least some of the respective light sensor elements are exposed to light passing unobstructed over the surface from the light source in the case that the surface is clear of the substance; and a processor arranged to receive signals from the sensor array, representing the amount of light falling on the plurality of light sensor elements, and arranged to detect therefrom the thickness of a substance deposited on the surface.

According to a further aspect of the present invention there is provided a method for detecting the depth of a deposition on a plate comprising the steps of: transmitting light over a surface of the plate; detecting the amount of light that has travelled over the plate; and determining, from the detected light, the depth of a deposition on the surface of the plate.

According to a yet further aspect of the invention, there is provided a method of detecting the thickness of a substance on a surface, comprising: shining light from a light source across the plate so that at least some of the light falls on a sensor array comprising a plurality of respective light sensor elements positioned at respective different distances in a direction transverse to the surface, subsequently reading out signals from the light sensor elements, and detecting the said thickness from the said signals.

In summary, aspects of the present invention may provide a monitoring system designed to detect the depth of deposition of a substance on a surface, such as the depth of dust in a ventilation shaft, the monitoring system including a light source and a sensor. The light source is arranged to transmit light across a detection surface and the sensor is on the other side of the detection surface. When a substance, such as dirt or grease, is deposited on the surface it obstructs the light and the amount of light reaching the sensor decreases. A processing means detects the decrease in light and from this the depth of the deposition on the surface can be calculated. Preferably the sensor comprises a CCD array, and the substance throws a shadow on the array. The processing means can then determine the depth of the substance from the position on the array of the edge of the shadow. Preferably the monitoring system is placed in a low power "sleep" mode in between intermittent operations for detecting the depth of the substance. In this way, it can be battery operated and the battery life is preserved.

Other aspects and features of the present invention will become apparent to those ordinarily skilled in the art upon review of the following description of specific embodiments of the invention in conjunction with the accompanying figures, in which.

Figure 1:
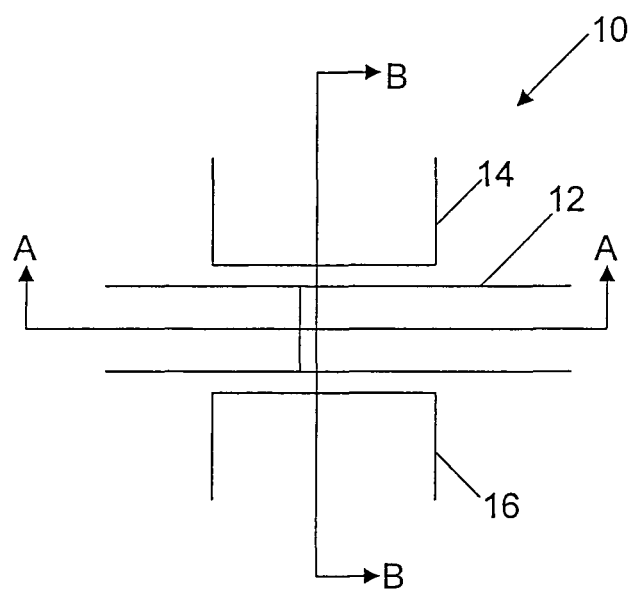
FIG. 1 is a plan view of a detector according to a first embodiment.
Figure 2:
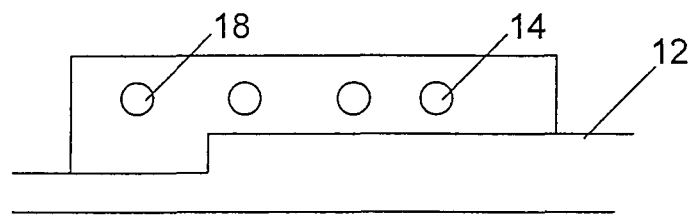
FIG. 2 is a cross-section along the line A-A of FIG. 1.
Figure 2A:
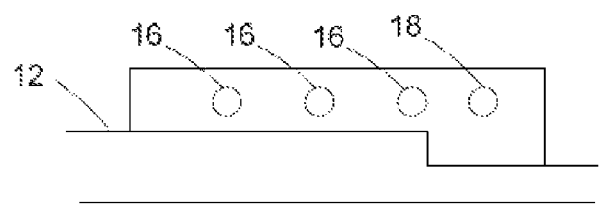
Figure 2B:
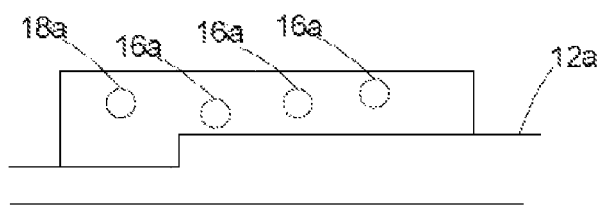
Figure 2C:
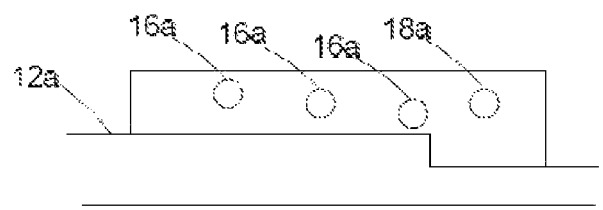
Figure 3:
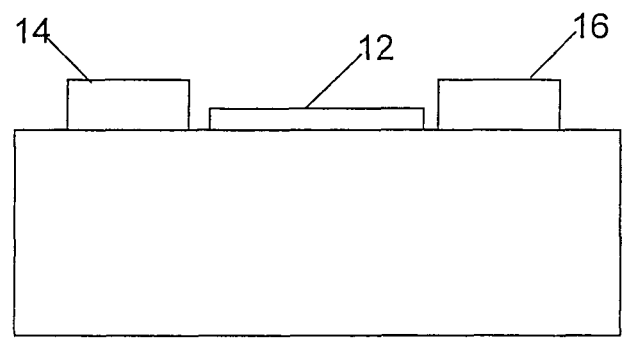
FIG. 3 is a cross-section along the line B-B of FIG. 1.

FIGS. 1 to 3 show a detector 10 in accordance with one embodiment of the present invention. The detector 10 has a plate 12 which provides a surface upon which substances, such as dirt and grease, are deposited as they travel through the duct. The plate 12 is preferably aligned with the duct in which the detector is placed so that any dirt deposited on the plate is the same depth as that on the wall of the duct.

The detector 10 also includes a light source 14 which transmits light and a sensor 16 that is positioned receive the light emitted by the light source 14. The light source 14 and sensor 16 are situated on either side of the plate 12 so that any light emitted by the light source 14 travels over the surface of the plate 12 which is exposed to the atmosphere in the duct.

To sense the depth of dirt present on the surface of the plate 12 the light source 14 transmits light across the plate 12 to the sensor 16. The light sensor detects the light, and transmits a signal representing the intensity of the received light to a processor (shown in FIG. 5).

The processor, upon receipt of the signal, determines whether the depth of dirt built up on the plate is great enough for the duct to be cleaned. The processor may achieve this, for example, by determining when the intensity of the light received by the sensor drops below a threshold level. The threshold level may be predetermined or may be automatically or manually adjusted. For example, the processor may include an input allowing a user to alter the threshold level. By allowing variation in the threshold, variation in the amount of light transmitted by a light source can be compensated for.

The threshold level may be a value of intensity or, alternatively, it may be a percentage of the light transmitted by the light source.

Alternatively, the processor may compare the intensity of the light transmitted with the light detected by the light sensor. This can be used to provide a reference point for the depth of the dirt present on the plate.

The processor may output the result of the determination using any suitable means. For example, the processor may compare the signal from the reference sensor to the signal received by the other light sensors. The difference may then be converted from an analogue signal to a digital signal using an analogue-to-digital converter. The resulting digital signal result may then be used to calculate a scalable reading on a display. Optionally, the digital signal may be used to give an approximate depth reading in microns.

The processor, once it has calculated the depth of the substance, may transmit the result to a user device, such as a workstation or mobile telephone or display the result on a user interface on the detector itself. In order to achieve this the device may be provided with a cellular phone circuit which transmits a digital value representing the dust level.

Optionally, the mobile telephone may be configured to forward any results received to other mobile telephones or to one or more designated email addresses for analysis purposes.

In a second embodiment the detector is substantially as described above but has a plurality of light sources and sensors as shown in FIG. 2. The plurality of light sources are situated on one side of the plate and the plurality of sensors are situated on the other as described above. Each sensor is preferably aligned with one of the sources in a sensor-source pair. The detector functions as described as above, however, instead of a single reading being used to determine whether the duct needs cleaning, the processor calculates an average value for the light received by the sensors and determines whether the average value is above or below the threshold.

Optionally, any of the detectors described above may be provided with a reference light source (18 in FIG. 2) and light sensor. The reference source and sensor are positioned above the plate at a great enough distance that the transmission of light between them is not obstructed by any dirt build-up on the plate. This may be achieved by increasing the distance between the plate 12 and the reference source and sensor by raising the reference source and sensor. Alternatively, this may be achieved by providing a step in the plate 12 as shown in FIG. 2.

As with the sources and sensors described above, the reference light source 18 transmits light across the plate 12 towards the reference light sensor (not shown). The sensor determines the intensity of the light received and transmits an output signal to the processor. The processor means can use this measurement as a maximum light intensity when determining the threshold. This is useful because the amount of light received by the light sensors may be reduced by particles in the air, such as fumes, or dust either in the air or on viewing windows meaning that the maximum amount of light to be received by the sensor is less than the intensity of the light transmitted by the light source.

Figure 4:
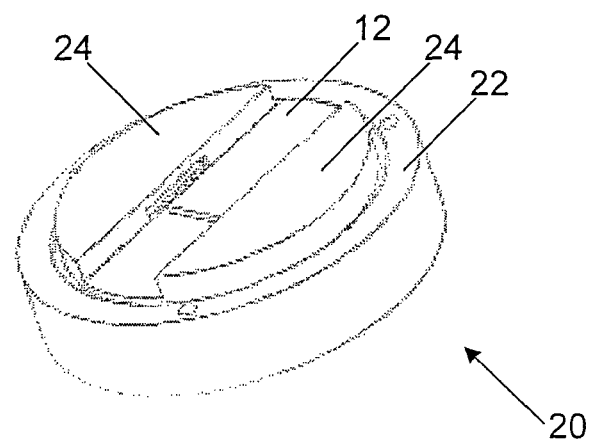
FIG. 4 illustrates a housing for the detector.

Preferably the detector is provided with a housing 20 as illustrated in FIG. 4. The housing 20 is provided with an outer flange 22 that allows it to be secured to the duct wall (not shown) so that the plate 12 may be generally flush with the inner surfaces of the duct wall. The light sources and detectors are contained in portions 24 that are slightly raised compared to the plate to allow the light to pass over the plate 12.

Figure 5:
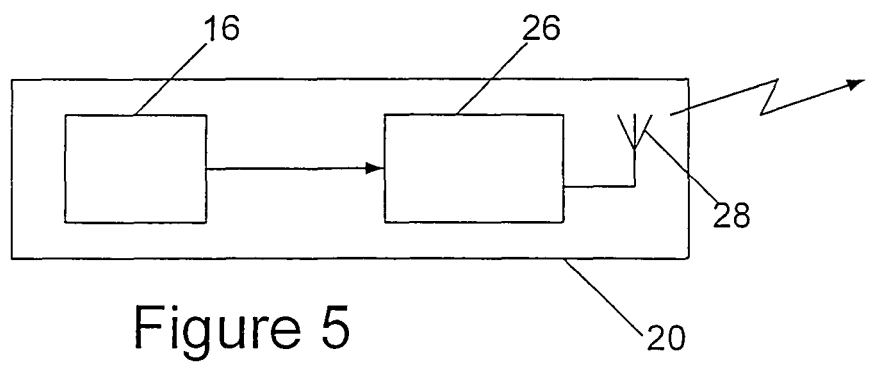
FIG. 5 shows the processor connected to the sensor.

As shown in FIG. 5, the processor 26 may be situated in the detector. Alternatively the processor may be located remotely from the light sources and sensors. In this arrangement the light sensors and processor may be connected physically, for example they may be connected by a wire. Alternatively, the sensors and processor may be wirelessly connected, with the light sensors transmitting their readings to an antenna to be transmitted to the processor. The transmission to the processor may, for example, be in the radio frequency domain. As mentioned previously, the apparatus may have an antenna 28 to enable the determination made by the processor 26, concerning the depth of the substance, to be transmitted wirelessly to a user interface.

The light sensors and sources may be arranged to transmit and detect light constantly. Alternatively, the light sensors and sources may be remotely activated using any suitable method. For example an infra-red signal may be used to activate the detector.

In another arrangement the detector may also include a timer. The detector may be arranged to cause the light sources and sensors to switch on after a time period has elapsed. The time period may be predetermined and programmed into the detector or, alternatively, the time period may be set by a control system. This is advantageous because it allows the period between sensing to be varied, because when the duct has just been cleaned it will not need to be checked for a long time, but the longer the duct has gone without cleaning the more frequently it should be checked. Preferably, the timer operates on a very low current.

The detector may be battery or mains powered.

Preferably the light transmitted by the light sources is pulsed. The pulses may have a frequency of approximately 65 kHz. Additionally, each pulse may last for only 160 microseconds. The light may be infra-red.

In a further embodiment, each light source and sensor pair may be a different distance from the plate. Each sensor transmits the amount of light it has detected to the processing means. The processor can then determine the sensors which are detecting light at an intensity below the threshold level and those which are detecting light above the threshold level. This allows the processing means to determine the depth of the dirt on the plate.

In yet another embodiment the sensors are replaced by a sensor array. The sensor array may be, for example an optical, charge coupled array. The array is divided into segments each of which is illuminated by a light source. When dirt has built up some of the segments in the array will sense the received light and others, below the level of the dirt, will detect a much lower light intensity. The array, as before transmits the output from each sensor to a processor which determines where there is a step change in the signal. The point of the step-change is the point at which the layer of dirt ends. From this the depth of the dirt on the plate can be determined.

The use of an array allows a more accurate determination of the depth of the build up. It is estimated that an output sensitivity of ±7.0 microns may be achieved if, for example, an array spacing of 7.0 microns is used.

Figure 6:
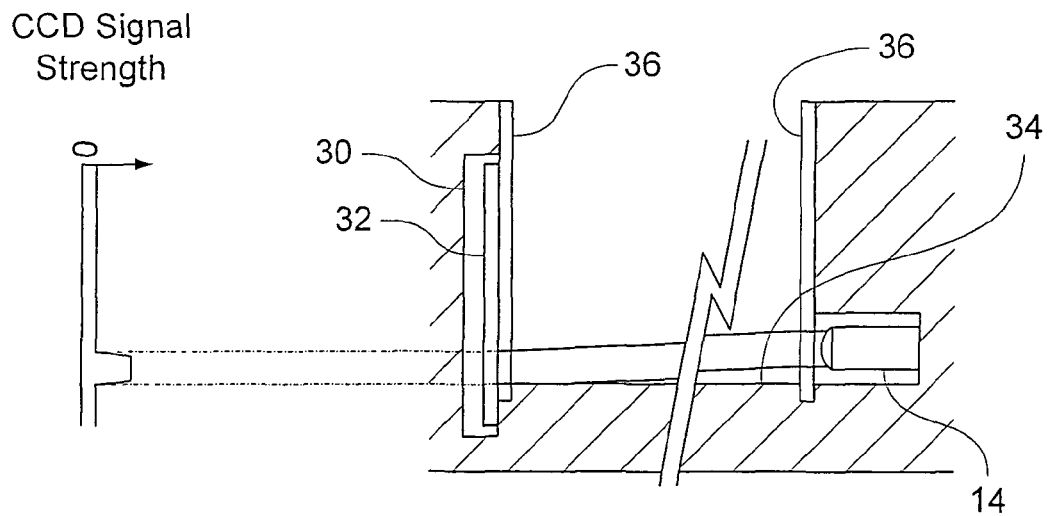
FIG. 6 is a cross-section, similar to FIG. 3, of part of a detector according to another embodiment of the invention.

An embodiment using a charge-coupled-device array will now be described in more detail with reference to FIGS. 6, 7a and 7b.

In this embodiment the sensors 16 are replaced by a single CCD sensor 30, having a CCD array 32 in which pixels are arranged at different heights relative to the surface 34 onto which dust or another substance may be deposited. A light source 14, such as an infra-red light emitting diode, illuminates a spot on the CCD array 32. The light source 14 is arranged so that part of the light from it is obstructed by the surface 34 when the surface is clean, so that the material (plate, shelf etc) that forms the surface throws a shadow onto the CCD array 32. Consequently, part of the CCD array 32 is not illuminated and will provide a low signal output. However, a high level output will be provided from the CCD pixels that are illuminated. The CCD output signal strength is shown at the left in FIG. 6, in line with the CCD array 32. This shows the high signal regional where the CCD 32 is illuminated, while the remainder of the CCD 32 provides a low signal output. The high signal regional has an abrupt edge where the shadow of the surface 34 falls on the CCD array. As dust builds up on the surface 34, the position of this shadow will move upwards on the CCD array 32, and accordingly the amount of dust (or other substance) deposited on the surface 34 can be determined from the CCD output by detecting the position of the edge of the shadow cast on to the CCD array 32.

As an example, the CCD device 30 may be a line imaging CCD from Hamamatsu Corporation (part number S10226), which has a CCD line array 32 that is 0.125 mm wide and has 1024 picture elements at a pitch of 7.8 µm. To match this, the light source 14 may be a Hamamatsu spot LED (part number L7868-02). This spot LED provides a very narrow beam, enabling the required part of the CCD array 32 to be illuminated with a high intensity. The two Hamamatsu devices are matched spectrally with each other, at 700 nm, enabling the maximum signal strength output for the minimum power consumption. This high efficiency together with the low operating voltages of the devices makes them suitable for use in a battery-powered device.

The gap between the light source 14 and the CCD array 32, which contains the surface 34, may be about 10 mm wide. This is much wider than is necessary for the device to operate to detect the thickness of the substance deposited on the surface 34. However, if the gap is narrower than this it becomes difficult to clean, and it is important in practice that the surface 34 is cleaned adequately at the time when the dust or grease layer within the duct as a whole is cleaned, or else the thickness of dust or other substance deposited on the surface 34 will cease to be a reliable proxy for the thickness of the dust or other substance deposited in the duct as a whole. The narrow beam from the Hamamatsu spot LED allows it to bridge this gap without excessive loss in beam intensity. In order to cast a sharp shadow from the surface 34 onto the CCD array 32, the LED 14 is arranged so that the beam is angled very slightly towards the surface 34 (preferably by less than 10°, more preferably less than 5° and preferably at least 1°, most preferably at about 2.5°). The LED 14 is positioned so that the angled beam intersects the last few millimeters of the width of the surface 34 (preferably no more than a third of the width of the surface 34 is illuminated and more preferably no more than a quarter). This ensures that a sharp shadow from the surface 34 is cast on the CCD array 32 while ensuring that most of the width of the beam reaches the array 32 so as to maximise the range of thicknesses of deposit on the surface 34 that can be measured.

During a measurement operation, the LED light source 14 is turned on briefly, to expose the CCD array 32. Then the pixel signals from the CCD array 32 are clocked out serially, and the output signal is analysed. The output signal, in the absence of any substance deposited on the surface 34, is shown in FIG. 7a (which is an enlarged version of the CCD output signal shown in FIG. 6). The signal obtained after a certain thickness of a substance has been deposited on the surface 34 is shown in FIG. 7b. As can be seen in FIGS. 7a and 7b, the CCD output signal is initially at a low level, corresponding to the pixels that are outside the area of the beam from the LED light source 14. The signal then has a rising edge corresponding to the edge of the light beam, followed by a falling edge corresponding to the edge of the shadow of the surface 34. As dust or another substance builds up on the surface 34, the position of this falling edge will shift, as the build-up of deposited substance causes the edge of the shadow to move. This is indicated by the distance between the two broken lines in FIGS. 7a and 7b. By measuring this shift, the depth of dust or other substance deposited on the surface 34 can be determined.

The initial position of this falling edge, when there is nothing deposited on the surface 34, is stored in the processor 26 as a zero-dust reference position. This may be a factory-set value, or it may be set during a calibration process when the detector device is initially installed in position, or it may be re-set each time the detector is cleaned. The shift, measured in number of pixels, of the falling edge of the CCD signal from this zero-reference position, enables the thickness of dust or other deposited substance to be calculated using the known pixel pitch of the CCD array 32.

The CCD output signal can be analysed by comparing the signal strength with a suitable reference value, so that the rising edge of the output signal is detected when the CCD output signal strength exceeds the reference value, and the falling edge is detected when the CCD output signal strength falls below the reference value. It is anticipated that this analysis method will be suitable in most circumstances, even though dust or other substance settling in front of the CCD array 32 and the light source 14 will also affect the signal strength, provided that a suitable reference value is chosen. However, if obscuration of the light source 14 or the CCD array 32, or some other factor, causes problems for an analysis method using a simple pre-set comparison value, other known signal processing techniques may be used to analyse the shape of the CCD output signal, in order to detect the position of the falling edge. For example, in each individual read-out operation the average of the ten lowest pixel output values may be taken as a minimum value and the average of the three highest pixel values may be taken as a maximum value, and a threshold may be set at half way between these two values in order to detect the rising and falling edges of the CCD output signal.

Figure 7A:
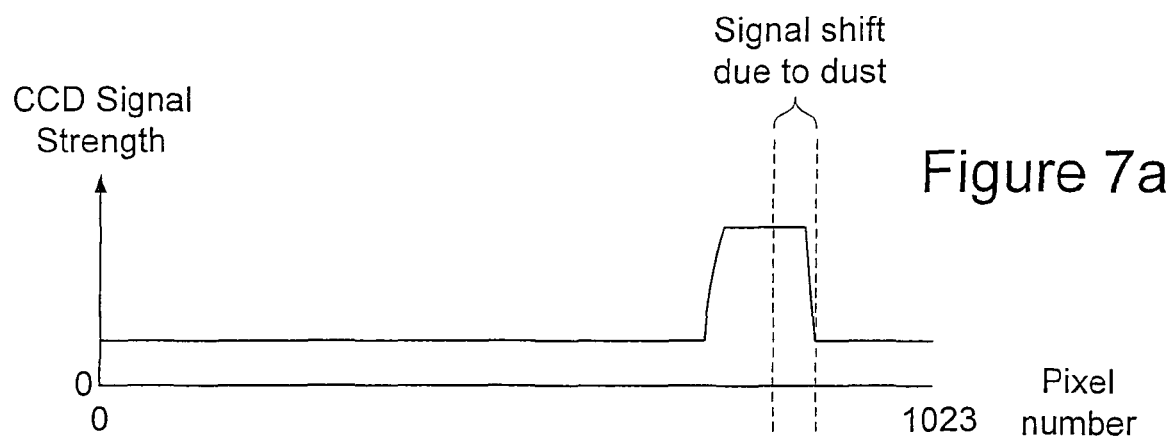
FIG. 7a shows an example of the signal read-out from the CCD array of the embodiment of FIG. 6 in the absence of any deposited substance.
Figure 7B:
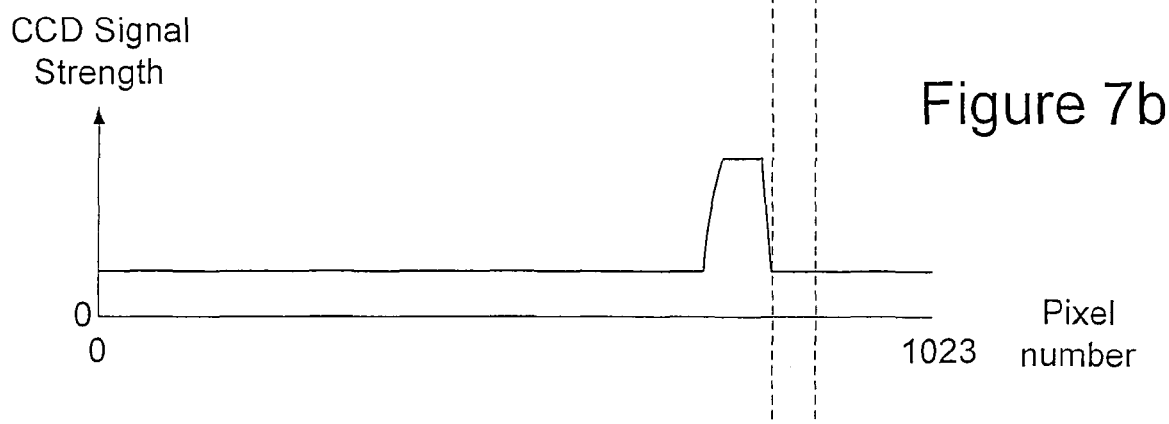
FIG. 7b shows an example of the signal read-out from the CCD array of the embodiment of FIG. 6 in the presence of some deposited substance.

As shown in FIGS. 7a and 7b, the rising and falling edges of the CCD output signal are not quite vertical. This arises for various reasons. For example, the intensity profile of the beam from the LED cannot be precisely a "top hat" shape and there will always be some falling off of beam strength at the edge. This affects the rising edge of the signal more than the falling edge, because the shadow of the surface 34 means that the edge of the beam is obscured and does not contribute to the falling edge of the signal. However, any translucence and light-scattering effect of the substance deposited on the surface 34 will cause the falling edge to be less abrupt. Additionally, the image is slightly blurred by the effect of protective glass layers 36 that cover the light source 14 and the CCD device 30 to protect them from dust and other substances. In order to minimise the blurring effect of the glass layers 36, they should be made as thin as possible and are preferably less than 1 mm thick, more preferably less than 0.5 mm thick and may for example be between 0.2 mm and 0.4 mm thick.

In this embodiment, the processor 26 acts as a control system for the detector as a whole, and controls the operations of the LED light source 14 and the CCD device 30, in addition to processing the CCD output and communicating the result to a user. Preferably, the processor 26 uses low power-consumption technology in which components can be placed in a "sleep mode" to reduce power when they are not in use. Microcontroller devices provided by Microchip Technology Inc. may be suitable for this purpose.

Preferably, the main controller in the processor 26 is a PIC 18F24K20 microcontroller from Microchip Technology Inc. When no action is required from the processor 26, the microcontroller enters a sleep mode in which the entire circuit consumes less than 2 µA. During the sleep mode, a low power 32 kHz clock is used to wake the microcontroller every 16 seconds. On waking, the microcontroller performs initial operations to determine whether full operation is needed. If full operation is needed, the system proceeds to wake up fully. Otherwise it goes back to sleep for another 16 seconds. The system can be programmed so that it wakes up fully only when a measurement is required of the thickness of the substance accumulated on the surface 34. This could be done for example once per day or once per week. Accordingly, the system is in its fully awake mode for only a tiny proportion of the total time, resulting in greatly reduced power consumption.

When a measurement is required, the microcontroller wakes up fully and uses a conventional crystal-based 16 MHz oscillator. It wakes up the radio system used for communication with a user, provides power to the CCD device 30, and then turns on the LED light source 14 briefly to expose the CCD array 32 (all of these parts are powered down while the microcontroller is in sleep mode). The CCD signal is clocked out serially and processed to obtain the height detection data. The detection data is transmitted by radio using an EmberNet wireless network to a GPRS controller that acts as a data sink. Provided that the data is sent successfully, the microcontroller shuts down the other components of the detector and returns to its sleep mode.

If the microcontroller receives an error message, indicating that the data has not reached the GPRS controller successfully, it shuts down the other components of the detector and returns to sleep mode in the same way, but it is set to wake up after four minutes to try to send the data again. In this way, the processor 26 attempts to send the data every four minutes until it is successful. Advantageously, the period required between measurement operations is transmitted to the processor 26 by the GPRS controller, enabling variation in the intervals between measurements both according to the detected height of the substance accumulated on the surface 34 and also according to other factors which may not be available to the microcontroller in the processor 26 of that particular detector, such as thickness measurements from other detectors in the same system or some other user requirement.

The EmberNet wireless network uses a simplified version of the ZigBee wireless protocol, and can be implemented using the ETRX2-PA transceiver from Telegesis (UK) Limited in the detector as part of the processor 26. This provides a wireless Personal Area Network, and the ETRX2-PA module is a high power module allowing the network to operate over an increased distance of, under ideal conditions, up to one mile from the transceiver module to the controller. In this way, a network can be provided made up of a plurality of separate detector devices and the controller. Each radio transceiver module has a unique identifier, enabling the controller to identify the corresponding detector device.

The ETRX2-PA transceiver module is controlled by the microcontroller in the processor 26, and is powered down when the microcontroller is not operating, so that this module also does not consume significant power when the detector device is in the sleep mode. Additionally, the radio transceiver module is able to detect the voltage of the supply battery and transmit this information to the network controller, enabling the end user to be informed when the battery of any individual detector needs to be changed.

In order to forward data from the EmberNet network to the end user, the EmberNet network is connected to a GPRS controller, which may for example use a Telit TGM620 GPRS modem and a Microchip PIC18F6620 microcontroller, enabling the EmberNet network to communicate with the end user via the cellular telephone network. In this way, a plurality of detectors may be arranged throughout a network of ventilation ducts or in some other installation in which it is desired to monitor the build up of a substance on a surface, and the outputs of the various sensors may automatically be sent to, and the sensors can be controlled from, the Information Technology system of the organisation responsible for monitoring the sensors.

The above embodiments are provided by way of non-limiting example and many alternatives and modifications will be apparent to those skilled in the art. Accordingly, the present invention should be regarded as covering all matter falling within the scope of the accompanying claims.

The invention claimed is:

1. A detector comprising:
   a. a plate;
   b. a light source positioned to transmit light over a surface of the plate;
   c. a light sensor positioned to detect light that has been transmitted by the light source and passed over the surface of the plate; and
   d. processing means arranged to determine whether the amount of light detected by the sensor is less than threshold, wherein the threshold is adjustable such that the depth of a substance on the plate can be determined.

2. A detector as claimed in claim 1 wherein the light sensor is a receiver array.

3. A detector as claimed in claim 2 wherein the processing means is arranged to determine the point of a step change in the light detected by the receiver array and thereby determine the depth of the substance on the surface of the plate.

4. A detector as claimed in claim 1 further including a plurality of light sources and light sensors, each light source having a corresponding light sensor.

5. A detector as claimed in claim 4 wherein the plurality of light sources and light sensors are disposed at differing distances from the plate; the processing means being arranged to determine the light sensors receiving an intensity of light above a threshold and to use the determination to calculate the depth of the surface.

6. A detector as claimed in claim 1 further including a reference light source and light sensor positioned a distance away from the plate such that the path of light between the reference light source and light sensor is not obstructed by the substance on the plate.

7. A detector as claimed in claim 1 wherein the processing means is arranged to determine the depth of the substance by determining when the amount of the light detected by the light sensor is below a threshold.

8. A detector as claimed in claim 7 when dependent upon claim 6 wherein the threshold is calculated as a percentage of the light received by the reference light sensor.

9. A detector as claimed in claim 1 wherein the detector includes a reference table including the intensity the light detected by the light sensor and the corresponding depth of substance, the processing means being arranged to consult the reference table and thereby determine the depth of the substance on the plate from the intensity of light detected by the light sensor.

10. A detector as claimed in claim 1 further including a timer, an activation means and a deactivation means; the detector being arranged to turn on using the activation means and turn off using the deactivation means after a period of time has expired.

11. A detector as claimed in claim 10 wherein the processing means alters the period of time according to the determined depth of substance.

12. A detector its claimed in claim wherein the processing means is located remotely from the plate, light source and light sensor.

13. A detector as claimed in claim 12 wherein signal representing the light detected by the light sensor is transmitted wirelessly.

14. A detector as claimed in claim 1 wherein the processing means is arranged to transmit the determination to a user interface.

15. A detector as claimed in claim 14 wherein the detector includes an aerial and the determination is transmitted to a user interface wirelessly.

16. A detector as claimed in claim 1 wherein the light source is arranged to transmit light in pulses at a pulse frequency of 65 kHz.

17. A detector as claimed claim 16 wherein the light source a said pulse has a duration of 160 microseconds.

18. A network comprising a plurality of detectors according to claim 1 arranged to communicate with a common device for receiving respective detected thicknesses of the substance from respective ones of the plurality of detectors.

19. A ventilation conduit including a detector according to claim 1.

20. A detector for detecting the thickness of a substance deposited on a surface, comprising:
   a surface on which a substance may be deposited;
   a light source arranged to shine light so that the light passes across the surface and, in the case that surface is clear of the substance, at least part of the light passes over the surface unobstructed;
   a sensor array comprising a plurality of respective light sensor elements positioned at respective different distances in a direction transverse to the surface, and at least some of the respective light sensor elements are exposed to light passing unobstructed over the surface from the light source in the case that the surface is clear of the substance; and
   a processor arranged to receive signals from the sensor array, representing the amount of light falling on the plurality of light sensor elements, and arranged to determine whether the amount of light detected by each of the light sensor elements is less than a threshold, wherein the threshold is adjustable, and detect therefrom the thickness of a substance deposited on the surface.

21. A detector according to claim 20 in which the sensor array comprises a charge-coupled device in which the said respective light sensor elements comprise respective CCD pixels.

22. A detector according to claim 20 in which the light source comprises a light-emitting diode.

23. A detector according to claim 20 in which the light source is arranged to shine the light in a substantially parallel-sided beam.

24. A detector according to claim 20 in which the surface is substantially planar.

25. A detector according to claim 20 in which the light source is arranged so that, in the ease that the surface is clear of the substance, part of the light intersects with at least a part of the surface.

26. A detector according to claim 25 in which the sensor is arranged so that, in the case that the surface is free of the substance, some of the said respective light sensor elements are in the shadow of the surface with respect to light from the light source.

27. A detector according to claim 20 in which the processor is arranged to detect the thickness of the substance deposited on the surface by detecting, from the signals received from the sensor array, the position on the sensor of a boundary between light sensor elements that are exposed to light from the light source and light sensor elements that are shaded from light from the light source.

28. A detector according to claim 20 in which the processor is arranged to transmit the detected thickness of substance wirelessly to a further device.

29. A detector according to claim 20 in which the processor comprises or is part of a digital control system that is arranged to perform repeatedly and intermittently a detection operation, in which the control system controls the light source to shine the said light and controls the sensor in to provide said signals to the processor and in which the processor detects the thickness of the substance, and the digital control system is arranged to enter a low-power-consumption state between repetitions of the detection operation.

30. A network comprising a plurality of detectors according to claim 20 arranged to communicate with a common device for receiving respective detected thicknesses of the substance from respective ones of the plurality of detectors.

31. A ventilation conduit including a detector according to claim 20.

32. A method for detecting the depth of a deposition on a plate comprising the steps of:
   a. transmitting light over a surface of the plate;
   b. detecting the amount of light that has travelled over the plate; and
   c. determining whether the detected light is less than a threshold, wherein the threshold is adjustable, such that the depth of a deposition on the surface of the plate can be determined.

33. A method of detecting the thickness of a substance on a surface, comprising:
   shining light from a light source across the plate so that at least some of the light falls on a sensor array comprising a plurality of respective light sensor elements positioned at respective different distances in a direction transverse to the surface,
   subsequently reading out signals from the light sensor elements;
   determining whether the amount of light detected by each of the light sensor elements is less than a threshold, wherein the threshold is adiustable; and
   detecting the said thickness from the said signals.

34. A method according to claim 33 in which the step of shining light comprises shining it at an angle and position such that some of the respective light sensor elements are in the shadow of the surface or would be in the shadow of the surface if it was clear of the substance.

35. A method according to churn 33 in which the step of detecting the thickness comprises determining the position on the array of the edge of a shadow of the substance cast on the array.

* * * * *